(12) United States Patent
Makshina et al.

(10) Patent No.: US 11,130,727 B2
(45) Date of Patent: Sep. 28, 2021

(54) PROCESS FOR THE PRODUCTION OF METHYL ACRYLATE FROM METHYL LACTATE

(71) Applicant: PURAC BIOCHEM BV, Gorinchem (NL)

(72) Inventors: Ekaterina Vladimirovna Makshina, Heverlee (BE); Bert Frans E. Sels, Heverlee (BE); Judit Canadell Ayats, Gorinchem (NL); Jan Van Krieken, Gorinchem (NL)

(73) Assignee: PURAC BIOCHEM BV

( * ) Notice: Subject to any disclaimer, the term of this patent is extended or adjusted under 35 U.S.C. 154(b) by 0 days.

(21) Appl. No.: 16/764,160

(22) PCT Filed: Nov. 13, 2018

(86) PCT No.: PCT/EP2018/081015
§ 371 (c)(1),
(2) Date: May 14, 2020

(87) PCT Pub. No.: WO2019/096761
PCT Pub. Date: May 23, 2019

(65) Prior Publication Data
US 2020/0377442 A1 Dec. 3, 2020

(30) Foreign Application Priority Data
Nov. 17, 2017 (EP) .................................... 17202434

(51) Int. Cl.
*C07C 67/327* (2006.01)
*B01J 29/40* (2006.01)
(Continued)

(52) U.S. Cl.
CPC ............. *C07C 67/327* (2013.01); *B01J 29/40* (2013.01); *B01J 37/06* (2013.01); *B01J 37/08* (2013.01);
(Continued)

(58) Field of Classification Search
None
See application file for complete search history.

(56) References Cited

U.S. PATENT DOCUMENTS

| 5,068,399 A | 11/1991 | Naito et al. |
| 2013/0157328 A1 | 6/2013 | Ozmeral et al. |
| 2015/0038735 A1 | 2/2015 | Ozmeral et al. |

FOREIGN PATENT DOCUMENTS

| CN | 101602010 A | 12/2009 |
| CN | 102001942 A | 4/2011 |

(Continued)

OTHER PUBLICATIONS

Zhang ("Catalytic dehydration of ethyl lactate over HZSM-5 modified with a transition metal" Huaxue Fanying Gongchen Yu Gongyi, vol. 25, issue 6, 2009, p. 571-575, including a machine generated English language translation thereof) (Year: 2009).*

(Continued)

*Primary Examiner* — Amy G Bonaparte
(74) *Attorney, Agent, or Firm* — Mendelsohn Dunleavy, P.C.

(57) ABSTRACT

The present invention is directed to a process for the production of methyl acrylate wherein methyl lactate is contacted with a ZSM-5 catalyst in the presence of methanol. It was found that the presence of methanol is essential to obtain a selective process with a high yield. With the process according to the invention methyl acrylate may be obtained as the major product of the reaction, especially if methanol is used as solvent instead of water, while acrylic (Continued)

Methyl lactate (ML) conversion compared to lactic acid conversion (LA) over K-ZSM-5 catalyst acid is detected in minor quantity (usually below 10 C %, but often below 5 C %). Methanol may be used as the sole solvent in the process, but preferably also a small amount of water is present in the solvent. In one aspect of the invention, between 1 and 25 wt % of water, based on the total amount of solvent is present.

20 Claims, 12 Drawing Sheets

(51) Int. Cl.
    *C07C 67/58*     (2006.01)
    *C07C 69/54*     (2006.01)
    *B01J 37/06*     (2006.01)
    *B01J 37/08*     (2006.01)
    *B01J 37/30*     (2006.01)

(52) U.S. Cl.
    CPC ............... *B01J 37/30* (2013.01); *C07C 67/58* (2013.01); *B01J 2229/186* (2013.01); *C07C 69/54* (2013.01)

(56) References Cited

FOREIGN PATENT DOCUMENTS

| | | |
|---|---|---|
| CN | 101703944 B | 5/2013 |
| CN | 104324746 A | 2/2015 |
| CN | 104399515 A | 3/2015 |
| CN | 104399519 A | 3/2015 |
| EP | 0379691 A1 | 8/1990 |
| WO | WO2013134385 A1 | 9/2013 |
| WO | WO2016201181 A1 | 12/2016 |

OTHER PUBLICATIONS

International Search Report and Written Opinion for corresponding International application No. PCT/EP2018/081015; dated Feb. 13, 2019 (12 pages).
Murphy, Brian M. et al., "Catalytic dehydration of methyl lactate: Reaction mechanism and selectivity control." Journal of Catalysis 339 (2016):21-30.
Yan, Bo, et al. "Potassium-Ion Exchanged Zeolites for Sustainable Production of Acrylic Acid by Gas-Phase Dehydration of Lactic Acid." ACS Catalysis 7.1 (2017): 538-550.
Zhang, Zhiqiang, et al. "Catalytic Performance and Characterization of Silica Supported Sodium Phosphates for the Dehydration of Methyl Lactate to Methyl Acrylate and Acrylic Acid." Industrial & Engineering Chemistry Research 48.20 (2009): 9083-9089.
Emeis, C. A. "Determination of Integrated Molar Extinction Coefficients for Infrared Absorption Bands of Pyridine Adsorbed on Solid Acid Catalysts." Journal of Catalysis 1412 (1993): 347-354.
Shi, Hai Feng, et al. "KNaY-zeolite catalyzed dehydration of methyl lactate." Chinese Chemical Letters 18.4 (2007): 476-478.
Zhang, Xianghui, et al. "Catalytic dehydration of lactic acid to acrylic acid over modified ZSM-5 catalysts." Chemical Engineering Journal 284 (2016): 934-941.
Notice of Reason for Refusal and Search Report for corresponding Japanese application No. 2020-524292; dated Jun. 21, 2021 (55 pages).
Yuan, Chuan, et al. "Alkali-metal-modified ZSM-5 zeolites for improvement of catalytic dehydration of lactic acid to acrylic acid." Chinese Journal of Catalysis 36.11 (2015): 1861-1866.
Zhan, Zhuo, et al. "Catalytic dehydration of ethyl lactate to ehtyl acrylate using Fe3+ modified HZSM-5." Huagong Keji (Science & Technology in Chemical Industry) 17.6 (2009): 1-5.

* cited by examiner

Figure 1A acrylic acid yield and Figure 1B lactic acid conversion with comparative catalyst 1A using conditions mentioned in WO 2016/201181, Figure 1C acrylic acid yield and lactic acid conversion for Na-ZSM5 catalyst using conditions mentioned in WO 2016/201181

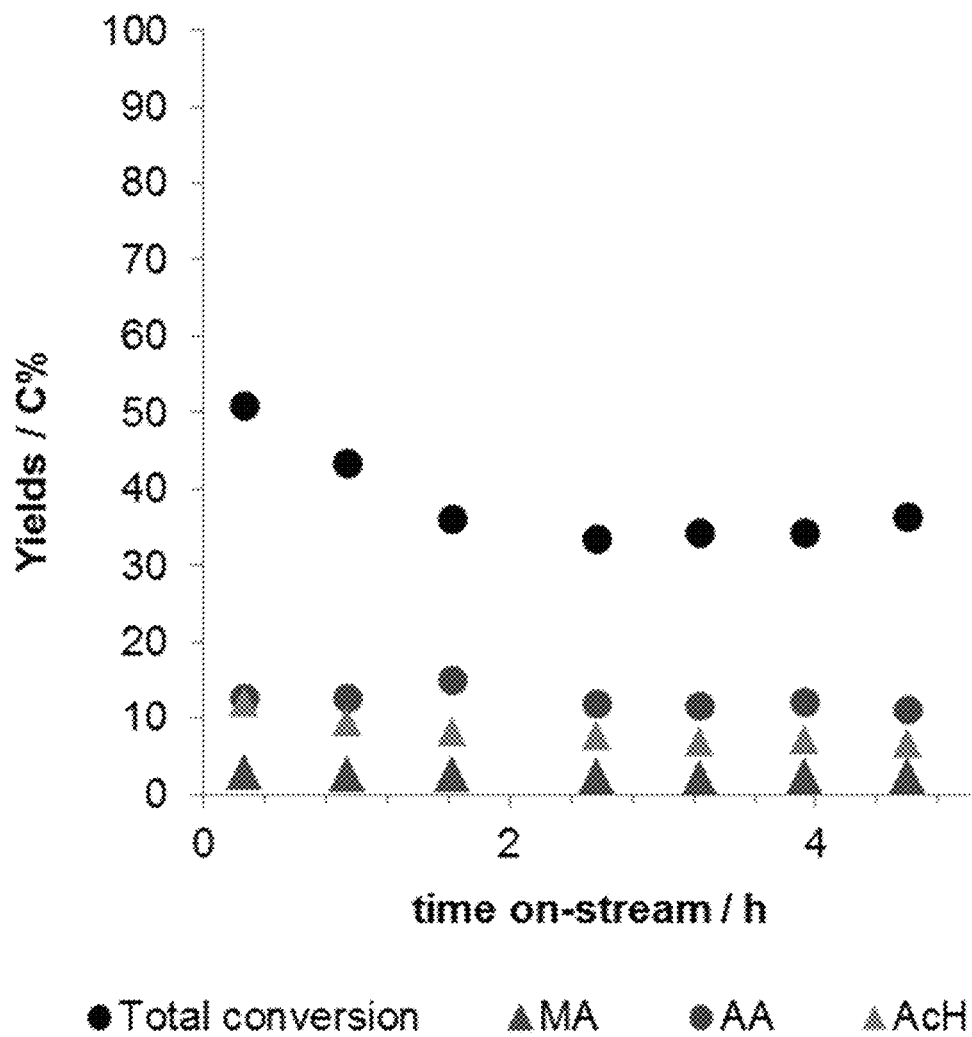
Figure 2: Methyl lactate (ML) conversion and methyl acrylate (MA) yield of comparative catalyst 1a using water as a solvent FIGURE 3A methyl lactate (ML) conversion, FIGURE 3B total acrylates selectivity of the KZSM-5 catalyst during 50h time-on-stream; FIGURE 3C product distribution (Yields are averaged within the period of stable acrylates (MA+AA) formation); FIGURE 3D impact of the water content of selectivity and stability of the KZSM-5 catalyst (35%ML/solvent feed)

FIGURE 4A Methyl lactate (ML)conversion and FIGURE 4B total acrylates selectivity over the KZSM-5 catalyst during 24h time-on-stream, influence of proton density.

FIGURE 5A Methyl lactate (ML) conversion and FIGURE 5B total acrylates selectivity (b) over the KZSM-5 catalyst during 24h time-on-stream, influence of K/Al molar ratio.

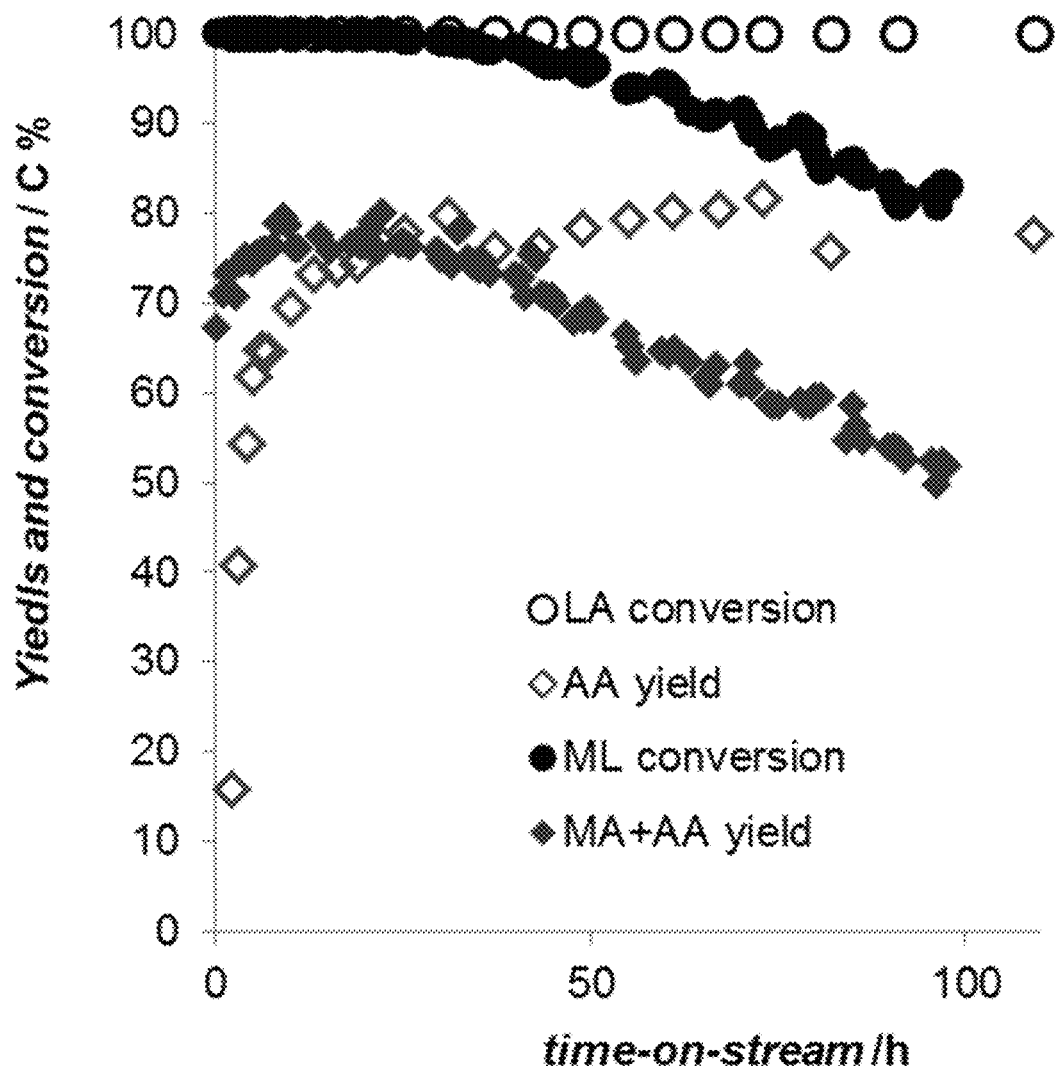
FIGURE 6. Methyl lactate (ML) conversion compared to lactic acid conversion (LA) over K-ZSM-5 catalyst

PROCESS FOR THE PRODUCTION OF METHYL ACRYLATE FROM METHYL LACTATE

FIELD

The present invention is directed to a process for the production of methyl acrylate from methyl lactate.

BACKGROUND

The shortage and price fluctuations of oil derived raw materials and the environmental awareness led to an extensive effort towards the development of alternative processes to produce chemicals from renewable (biobased) resources. The search towards new green polymers is challenging, however main current activities are concentrated on finding new synthesis routes for producing important drop-in chemicals and polymer building blocks. Among the extensive list of chemicals of industrial interest, acrylic acid gained high attention due to its market size and growth perspectives. Catalytic dehydration of lactic acid is an attractive route for the production of bio-based acrylic acid. Currently, most lactic acid conversion studies are focused on this reaction. According to the thermodynamic analysis, both lactic acid and esters could be used to produce acrylates (acid and/or esters). However, decomposition of the starting substrates via decarboxylation/decarbonylation pathways into acetaldehyde and carbon oxides is a more favorable process and thus the choice of appropriate catalysts is very important in order to still reach high acrylates yield.

Large variety of the solid catalysts have been applied as catalysts for the production of acrylates from lactic acid and esters such as phosphates and sulfates as bulk compounds and also supported over inert supports (e.g. silica and activated carbon), and zeolite-based materials. Based on the studies of the reaction mechanism, it has been suggested that the formation of the intermediate lactate salt with surface cations is an essential step. From this perspective, the use of zeolites as catalysts looks very promising since they possess a large number of cations in ion-exchange positions easily accessible for the organic substrates due to ordered porous structure of the silica-alumina framework. While most of the studies of zeolite application for acrylate formation from lactic acid are focused of the use of NaY and NaX zeolites, a few recent publications showed that other zeolites, e.g. L zeolite, ZSM-22, ZSM-35, MCM-22, ZSM-11, could be also used, but ZSM-5 and β-zeolite have highest potential.

Examples of publications that describe the production acrylic acid from lactic acid in the presence of a zeolite-based catalyst are cited below. For instance, in ACS Catal. 7 (2017) 538-550 and CN 104399519 the gas-phase dehydration of lactic acid to acrylic acid in the presence of a catalyst is described. ZSM-5 or beta zeolite is preferred. It teaches that a lower silica/alumina molar ratio leads to better acrylic acid selectivity, a higher yield and an improved stability. The silica/alumina molar ratio used is between 20-50. A hydrogen or sodium-form zeolite is subjected to 4 times ion-exchange with $NaNO_3$, filtered, dried and calcined. Subsequently the sodium zeolite is ion exchanged with KBr, filtered, dried and calcined.

In Chem. Eng. J. 284 (2016) 934-941 the lactic acid conversion to acrylic acid in the presence of a ZSM-5 catalyst is studied. To this end a HZSM-5 is treated with NaOH and subsequently impregnated with $Na_2HPO_4$. It is concluded that the NaOH treatment lowers the weak acidity sites. Phosphate treatment lowers the acidity slightly and increases the selectivity towards acrylic acid.

CN 104324746 describes the catalytic conversion of lactic acid to acrylic acid using ZSM-5 with a Si/Al molar ratio of 75 which has been modified with sodium and/or another cation such as potassium. The zeolite has been modified by ion-exchange with a metal ion solution, stirring, drying at 100-140° C. and calcination.

CN104399515 describes the catalytic conversion of lactic acid to acrylic acid using ZSM-5 which has been modified with an alkali treatment of 10 hours at 80° C. with 0.5 M NaOH, followed by a cation treatment and a sodium phosphate treatment.

In CN101602010 a quite harsh alkali treatment of ZSM-5 is described followed by phosphate impregnation. This catalyst is used for the conversion of lactic acid to acrylic acid.

WO 2016/201181 is directed to the catalytic preparation of alpha, beta-unsaturated carboxylic acid (such as acrylic acid) and/or esters thereof from an alpha-hydroxycarboxylic acid (such as lactic acid) or beta-hydroxycarboxylic acid and esters thereof. It mentions that all types of zeolites are suitable as catalyst, as long as it has surface acidity. ZSM-5 with a silica/alumina molar ratio of 10-100 is preferred. The non-framework cations may be virtually any known cation such as $H^+$, $Na^+Mg^{2+}$, $K^+$, $Ca^{2+}$ etc. These non-framework cations may be introduced by ion exchange. In the examples and description only ion-exchange of a H zeolite or $NH_4$ zeolite with sodium is described. Said NaZSM-5 may subsequently be impregnated with $K_2HPO_4$.

Thus, most publications are directed to the conversion of lactic acid to form acrylic acid. In WO 2016/201181 the conversion of alpha-hydroxycarboxylic acid (such as lactic acid) or beta-hydroxycarboxylic acid and esters thereof is mentioned in general, only the conversion of lactic acid is actually described. The subject of the present invention is a process for the production of methyl acrylate (MA) from methyl lactate (ML). Compared to lactic acid (LA), methyl lactate is hardly studied. However, the use of methyl lactate (ML has many important advantages compared to the acid. First alkyl esters may be formed during the purification of the lactic acid produced by fermentation, moreover they can be synthesized over heterogeneous catalysts directly from sugars. It should be also emphasized that beside acrylic acid (AA), methyl acrylate (MA) is also an important acrylic monomer with worldwide annual production of 200 000 tons/year and it is mostly prepared by esterification of AA. Methyl acrylate finds applications in many fields such as in the production of coatings, elastomers, adhesives, thickeners, amphoteric surfactants, fibers, plastics, textiles and inks. When used in latex paint formulations acrylic polymers have good water resistance, low temperature flexibility and excellent weathering and sunlight resistance. In these applications methyl acrylate is often used as a comonomer in the polymerization with a variety of acrylic and vinyl monomers. When using methyl acrylate as comonomer, the resulting acrylic paints are harder and more brittle than those with the homologous acrylates. Copolymerizing methyl acrylate with acrylonitrile improves their melt processability to fibers. Methyl acrylate is the precursor to fibers that are woven to make carpets.

Methyl acrylate is also used in chemical synthesis. For instance, MA is used for the preparation of 2-dimethyl aminoethyl acetate. Methyl acrylate can be the starting material to make higher alkyl acrylates (e.g. ethyl acrylate, propyl acrylate, butyl acrylate) by transesterification reaction with alkyl alcohols.

Methyl acrylate can be converted to acrylic acid by hydrolysis.

Some publications are known that describe the conversion of methyl lactate to methyl acrylate with the help of a catalyst. However, the catalysts used herein are either susceptible to very fast deactivation, or give a low yield. See for instance, EP 0379691 which uses a 13X zeolite that is susceptible to fast deactivation, CN 102001942 that describes the use of Li-montmorillonite/NaY catalyst, with low yields of maximally 54%, H. F. Shi et al. Chinese Chemical Letters, 18 (2007) 476 that describes the use of KNaY zeolite that gives low yields, or Zhang, Z. et al. Ind. Eng. Chem. Res. 48 (2009) 9083-9089 which describes the use of Na-phosphates on $SiO_2$, which process also provides low yields.

We have found that the reaction of methyl lactate to methyl acrylate behaves totally different from the reaction of lactic acid to acrylic acid and therefore requires a different catalyst and reaction conditions.

SUMMARY OF THE INVENTION

The present invention is directed to a process for the production of methyl acrylate wherein methyl lactate is contacted with a ZSM-5 catalyst in the presence of methanol. It was found that the presence of methanol is essential to obtain a selective process with a high yield. With the process according to the invention methyl acrylate may be obtained as the major product of the reaction, especially if methanol is used as solvent instead of water, while acrylic acid is detected in minor quantity (usually below 10 C %, but often below 5 C %). Methanol may be used as the sole solvent in the process, but preferably also a small amount of water is present in the solvent. In one aspect of the invention, between 1 and 25 wt % of water, based on the total amount of solvent present, can be introduced to feedstock solution.

With the term "solvent" is meant the diluent that is used for the liquid feedstock.

In one aspect of the invention the ZSM-5 catalyst has a $SiO_2/Al_2O_3$ molar ratio of between 10 and 30.

In one aspect of the invention the ZSM-5 catalyst is a potassium form of ZSM-5 zeolite prepared by ion-exchange procedure. Preferably the potassium exchange degree is higher than 0.90, preferably higher that 0.95, most preferably higher than 0.97.

It is preferred to use a catalyst wherein the amount of Brønsted acid sites in the K-ZSM-5 catalyst as measured by FTIR on absorbed pyridine, is below 1 micromole/g. The preferred amount of Lewis acid sites, as measured by FTIR on absorbed pyridine is between 50 and 130 micromole/g, preferably between 86 and 100 micromole/g. The K/Al molar ratio of the catalyst is preferably between 0.95 and 1.00 (including 1.00), more preferably between 0.97 and 1.00 (including 1.00).

In another aspect of the invention the phosphorus content of the ZSM-5 catalyst is below 10 ppm. When using a catalyst that has been impregnated with a phosphorus compound such as K-phosphate salts, the activity and stability and selectivity of the catalyst is detrimentally affected.

In another aspect of the invention the sulfur content of the ZSM-5 catalyst is below 10 ppm. When using a catalyst that has been impregnated with a sulfur compound such as K-sulfates salts the activity and stability and selectivity of the catalyst is detrimentally affected.

In an aspect of the invention the catalyst has been prepared by ion-exchanging a sodium- or ammonium form of ZSM-5 with potassium chloride or potassium nitrate, filtering, washing, drying and calcining the ion-exchanged catalyst.

Optimally the starting material for the potassium salt ion exchange is a sodium-based ZSM-5 catalyst, but also the hydrogen or ammonium form may be used as starting material.

The catalysts used in the process according to the invention were found to be stable and highly selective towards the formation of methyl acrylate.

In an embodiment a methyl lactate solution in methanol, evaporated in inert gas is continuously led over a fixed catalyst bed, the product stream is isolated, separated and purified.

The resulting methyl acrylate is further processed by means of one or more distillation and/or extraction steps or any combination thereof.

The resulting methyl acrylate may also be hydrolyzed into acrylic acid. Optionally, said thus obtained acrylic acid is further processed by means of one or more distillation steps or extraction steps or any combination hereof.

BRIEF DESCRIPTION OF THE SEVERAL VIEWS OF THE DRAWINGS

FIG. 2 shows the methyl lactate (ML) conversion and methyl acrylate (MA) yield of comparative catalyst 1a using water as a solvent obtained in Comparative Example 3.

FIG. 6 shows the methyl lactate (ML) conversion compared to lactic acid conversion (LA) over K-ZSM-5 catalyst obtained in Example 7.

DETAILED DESCRIPTION OF THE INVENTION

Figure 1A:
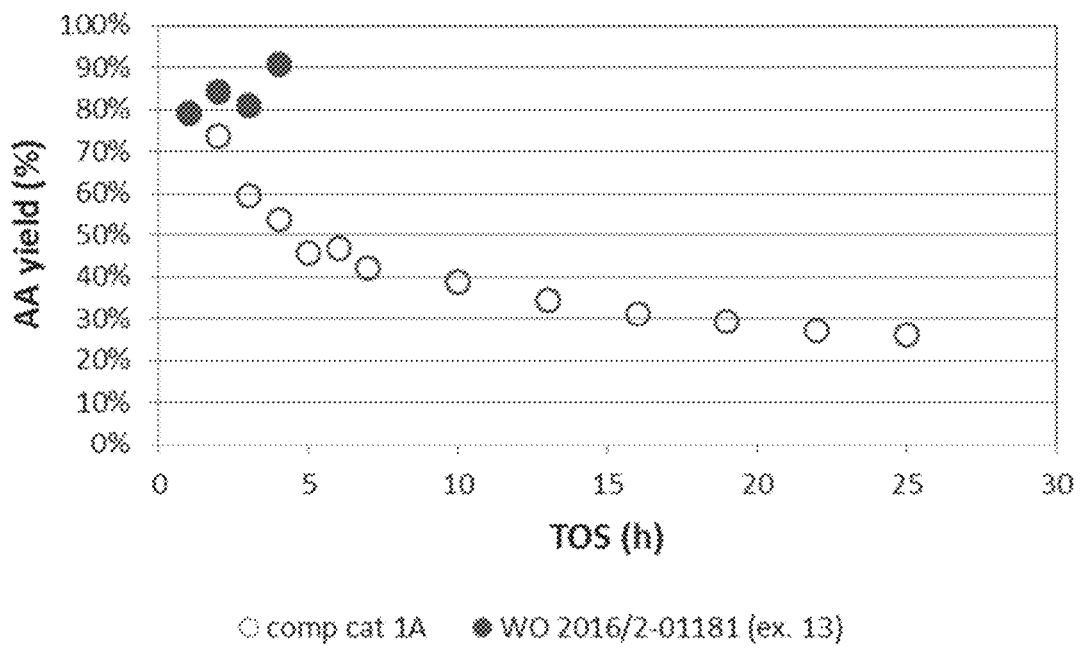
FIG. 1A shows the acrylic acid yield with comparative catalyst 1A using conditions mentioned in WO 2016/201181 obtained in Comparative Example 1, wherein the open circles and shaded x-es refer to the data obtained in our measurements and the filled circles and black-x-es refer to the data provided in WO 2016/2-01181, respectively.

The present invention is directed to a process for the production of methyl acrylate wherein methyl lactate is contacted with a ZSM-5 catalyst in the presence of methanol. It was found that the presence of methanol is essential to obtain the desired selectivity towards methyl acrylate with low amounts of side products. With the process according to the invention methyl acrylate may be obtained as the major product of the reaction, while acrylic acid is detected in minor quantity (usually below 10 C %). Methanol may be used as the sole solvent in the process, but preferably also a small amount of water is present in the solvent. In one aspect of the invention, between 1 and 25 wt % of water, based on the total amount of solvent present, can be added to liquid feedstock. It was found that this increases the stability of the conversion and slightly the selectivity towards methyl acrylate.

The catalyst used in the process according to the invention is ZSM-5 zeolite. This catalyst has the correct pore structure for the process presently envisaged. Preferably a catalyst is used wherein the $SiO_2/Al_2O_3$ molar ratio of the ZSM-5 is between 10 and 30. Beside the structural aspects of ZSM-5 zeolites, it was found that this catalyst has the best starting point for setting the amount of Lewis acid sites and Brønsted acid sites, which as will be explained below have a large impact on the selectivity and stability of the catalyst in the process.

In order to increase the selectivity of the catalyst for the production of methyl acrylate, a ZSM-5 catalyst is used that is a potassium-salt ion exchanged ZSM-5 catalyst. Usually a commercially available sodium-, hydrogen- or ammonium forms of ZSM-5 zeolite is subjected to one or several ion exchange steps with a potassium salt to create a potassium-exchanged ZSM-5 catalyst. Preferably the starting material is a sodium form ZSM-5, because this starting material is more susceptible to high level of ion-exchange and because there is less risk for residual Brønsted acidity. Residual Brønsted acidity (a higher proton density) was found to be detrimental to the stability of the catalyst. With the stability of the catalyst is meant the ability to run the process for a long period of time without extensive lowering of the yield. With a long period of time in this context is meant between 24 and up to 60 hours or even higher.

It was further found that the exchange degree determines the selectivity to methyl acrylate. With potassium exchanged catalyst a selectivity of above 75% could be obtained, with even a constant selectivity of about 80% for more than 24 hours on stream when using a potassium exchange degree of 1.00. The exchange degree is defined by the amount of potassium divided by the total amount of potassium and sodium. Preferably a catalyst is used that has a potassium exchange degree that is higher than 0.90, preferably higher that 0.95, most preferably higher than 0.97. In general, it is desired that the amount of Lewis acid sites is between 50 and 130 micromole/g, preferably between 86 and 100 micromole/g. This Lewis acidity may be measured by FTIR of absorbed pyridine.

As described above, it is desired that the amount of Brønsted acid sites in the ZSM-5 catalyst used is low; A proton density of less than 1 micromole/g is desired. It was found that with a value above 1 micromole/g even the selectivity of an essentially Na-free K-ZSM-5 catalyst is drastically lowered resulting in a less stable catalyst. The Brønsted acidity may be measured by FTIR on absorbed pyridine.

It was found that phosphorous treatment by for instance impregnation with phosphoric acid salts is detrimental for the activity and stability of the catalyst for methyl acrylate formation. Therefore, it is preferred that a catalyst is used wherein the phosphorus content of the ZSM-5 catalyst is below 10 ppm.

The same can be said for sulfurous treatment such as with sulfuric acid salts. It is preferred that a catalyst is used wherein the sulfur content of the ZSM-5 catalyst is below 10 ppm.

In general, the catalyst used for the process according to the invention may be prepared by ion-exchanging a sodium-, hydrogen- or ammonium form of ZSM-5 with potassium salt, washing, drying and calcination of the ion-exchanged catalyst. Optimal results are obtained when using a sodium form ZSM-5 catalyst.

The ion exchange step may be performed in any conventional way, for example by stirring the zeolite powder in an aqueous solution of salt, followed by filtration of mater/mother liquor, washing and drying. Preferably the temperature maintained during the ion-exchange step is at room temperature such as between 15 and 25° C. The concentration of the ion-exchange salt solution may be adjusted to the situation at hand, but normally between 0.5 to 1 M solutions may be used. Any suitable water-soluble potassium salt may be used. Preferred are KCl, $KNO_3$. As mentioned above, the use of phosphorous- or sulfur-containing salts is not advised. As described above, also multiple ion exchange steps may be conducted.

The washing step is done with water using a liquid/solid ratio of between 20 and 100, preferably between 30-80. The liquid/solid ratio is defined by the amount of liquid in ml per gram of zeolite powder. It was found that proper washing is important, because residual salts in the catalyst may give rise to an excess of cations in the catalyst resulting in a decreased stability and selectivity for methyl acrylate. Therefore, the use of a catalyst with a K/Al molar ratio of 1.00 is or just below 1.00 is preferred. Too extensive washing should be also avoided since it may lead to protonation and Brønsted acidity above 1 micromole/g.

After washing the catalyst is dried at elevated temperature, i.e. between 40 and 100° C., preferably between 50 and 70° C.

The calcining is performed at a temperature between 500 and 600° C., preferably between 500 and 550° C. for about 3-6 hours.

The process may suitably be conducted in continuous gas-phase reactor using a methyl lactate solution in methanol as a feedstock that has been evaporated in inert gas such as nitrogen gas over a fixed catalyst bed and isolating, separating, and purifying the product. Most convenient purification methods comprise distillation, extraction or one or more combinational steps thereof. Also, other conventional purification techniques, such as adsorption e.g over an alumina, silica or carbon column, may be used either alone or in combination with the previously mentioned purification methods. In view of the difference in boiling points of the common impurities such as acrylic acid and acetaldehyde, distillation is the most preferred purification technique. The preferred reaction temperature is between 300 and 400° C. using atmospheric pressure.

The resulting methyl acrylate may also be hydrolyzed into acrylic acid. Optionally, said thus obtained acrylic acid is further processed by means of one or more distillation steps or extraction steps or any combination hereof.

The present invention is further illustrated by means of the following examples. These examples merely function to illustrate the invention and by no means can be construed as being limitative.

EXAMPLES

Procedure of the Catalytic Testing Used for the Catalytic Testing in Comparative Examples 1-2

20 wt % of lactic acid in water was used as substrate. The catalytic conversion of lactic acid was carried out in a fixed bed continuous downstream flow reactor. The reaction was performed at 330° C. and atmospheric pressure. Typically, 1 g of catalyst (1.65 ml), pelletized to a 0.25-0.5 mm fraction, was used. In order to avoid thermal decomposition of substrates and products in the reactor, a quartz reactor tube was filled with quartz wool below a catalyst bed and with glass beads above the catalyst bed. Blank tests at reaction temperature without catalyst have been conducted and no significant level of conversion was detected during these tests. The feed solution was pumped in the system using HPLC pump (Waters 515 HPLC pump, feed flow rate 0.05 ml/min) and mixed with $N_2$ to ensure complete evaporation (gas flow of nitrogen gas 27.5 ml/min). The Liquid Hourly space velocity (LHSV) was set to 1.8 $h^{-1}$.

The gaseous mixture was cooled and the liquid stream was analyzed off-line by gas chromatography (GC) equipped with a Stabilwax-DA column (30 m×0.32 mm ID×0.10 μm df, Restek), cold-on-column injector and a TCD detector.

Total conversion (TC, C % based on ML fed) was calculated according the equation:

$$TC = \frac{n_{LA(fed)} - n_{LA(left)}}{n_{LA(fed)}} \cdot 100.$$

Yields (Yi) of the products were calculated according the equation:

$$Y_i = \frac{n_{x_i}}{A_{LA(fed)}} \cdot 100$$

selectivity (S) toward i-product was calculated as follows:

$$S_i = \frac{Y_i}{TC} \cdot 100,$$

where $n_{x_i}$ is an amount of moles of i-product and TC is the LA conversion.

Catalytic Testing for Comparative Example 3 and Examples 2-6

98 wt % methyl (S)-lactate (Purasolv ML/ex Corbion) was used as substrate. Methanol, water-methanol or water were used as solvents for methyl lactate (ML) dilution. The catalytic conversion of methyl lactate to methyl acrylate was carried out in a fixed bed continuous downstream flow reactor. The reaction was performed at 320-340° C. and atmospheric pressure. Typically, 1 g of catalyst (1.7 ml), pelletized to a 0.25-0.5 mm fraction, was used. In order to avoid thermal decomposition of substrates and products in the reactor, a quartz reactor tube was filled with quartz wool below a catalyst bed and with glass beads above the catalyst bed. Blank tests at reaction temperature without catalyst have been conducted and no significant level of conversion was detected during these tests. Methyl lactate solution was pumped in the system using HPLC pump (Waters 515 HPLC pump) and mixed with $N_2$ to ensure complete evaporation.

Products were analyzed by on-line gas chromatograph (GC) equipped with a CPWAX 52CB column (20 m×0.25 mm×0.20 μm) and an FID detector. Carbon balance was calculated as total carbon amount in the analyzed products, divided by the total amount of carbons fed. Total conversion (TC, C % based on ML fed) was calculated according the equation:

$$TC = \frac{n_{ML(fed)} - n_{ML(left)}}{n_{ML(fed)}} \cdot 100.$$

Yields (Yi) of the products were calculated according the equation:

$$Y_i = \frac{n_{x_i}}{A_{ML(fed)}} \cdot 100$$

selectivity (S) toward i-product was calculated as follows:

$$S_i = \frac{Y_i}{TC} \cdot 100,$$

where $n_{x_i}$ is an amount of carbon moles (C moles) of i-product.

Characterization Techniques

IR experiments were performed on a Nicolet 6700 spectrometer equipped with a DTGS detector (128 scans; resolution of 2 $cm^{-1}$). Self-supporting wafers were pretreated in vacuum at 400° C. K for 1 h (5° C./min) before measurements. Acidity of the catalysts was analyzed using pyridine as probe. After pretreatment at 400 K, the samples were saturated with about 28 mbar of pyridine vapor at 50° C. for 20 min. The evacuated samples containing the adsorbed pyridine were heated up to 150° C., kept for 20 min and then IR spectra were recorded. The integrated molar extinction coefficients used in acidity quantification were 1.67 cm/micromole and 2.22 cm/micromole for the 1545 $cm^{-1}$ band characteristic for Brønsted acid site and 1455 $cm^{-1}$ band characteristic for Lewis acid site respectively (according to the data reported in C. A. Emeis, J. Catal. 141 (1993) 347-354)

Elemental composition was measured by IPC AES. 100 mg of dry powder was mixed with 500 mg of lithium borate ($LiBO_3$). Powder mixture was then transferred into graphite melting pot and placed in the muffle oven at 1000° C. for 10 min. Obtained melt was immediately transferred to the plastic beaker containing 50 ml 0.42M $HNO_3$ and kept under vigorous stirring for another 10 min. Next, probes were diluted 1/10 with 3 wt % $HNO_3$ aqueous solution and measured by IPC AES (Varian 720-ES). SRM (Standard Reference Material with certified concentrations of the elements of interest with codes AGV-1, PRI-1, BCS-267 and BCS-269 as specified at GeoReM, http://georem.mpchmainz.gwdg.de/) powders were used as standards. SRM powders were subjected to the same digesting procedure as zeolite powders and prepared solutions were used for calibration curves.

Example 1. Preparation of the Catalysts

Cat 1 to cat 6: K-exchanged ZSM-5 catalysts with different degree of ion-exchange were prepared by subjecting the parent NaZSM-5 zeolite with $SiO_2/Al_2O_3$ molar ratio of 24 (SN27, Alsi Penta) to an ion-exchange step wherein the zeolite powder was stirred in an aqueous solution of potassium nitrate ($KNO_3$) using varying concentrations of potassium nitrate and/or liquid to solid ratios specified in TABLE 1. The then obtained material was filtered and washed with Millipore Q water in order to remove the remaining salts using liquid to solid ratio of 60. Then samples were dried at 60° C. overnight and calcined in a muffle oven at 550° C. for 4 h in static air with the ramp of 3° C./min. The physico-chemical properties of the catalysts are given in TABLE 1. As the table shows, an increase of potassium exchange degree lead to substantial decrease of proton density (measured by IR of adsorbed pyridine, $NH_3$-TPD is not sensitive and not distinctive) and Lewis acidity (also measured by IR of adsorbed pyridine).

Cat 7 was prepared according to the procedure given above for Cat 6, but $KNO_3$ salt was replaced by sodium nitrate ($NaNO_3$).

Cat 8 was prepared via a 4-step exchange procedure at elevated temperature as described in Yan et al. [ACS Catal. 7 (2017) 538-550]. Air-dry zeolite powder was stirred in aqueous solution of 0.5 M $NaNO_3$ for 1 h at 80° C. using liquid to solid ratio of 20. Next, the zeolite was filtered, washed with Millipore water, and dried at 60° C. overnight. The same procedure was repeated 4 times. Finally the sample was calcined in a muffle oven at 500° C. for 3 h in static air with the ramp of 3° C./min.

The properties of the catalysts Cat 7-8 are given in TABLE 1. It shows that ion-exchange with Na-salt is not efficient to remove all residual protons. The multistep ion-exchange lead to increase of Brønsted acidity, possibly due to protonation during the multiple washing step.

Specific catalysts with increased proton density were prepared to illustrate the impact of the protons on the catalytic behavior.

Cat 9 was synthesized by a double ion-exchange procedure. In this case air-dry zeolite powder was stirred in aqueous solution 1M $KNO_3$ for 6 h (using liquid to solid ratio of 40), filtered and washed, dried at 60° C. overnight. The ion-exchange procedure was repeated twice without intermediate calcination step. The drying and calcination procedures were the same as for Cat 6.

Cat 10 was prepared by the same procedure as Cat 9 but ammonium hydroxide $NH_4OH$ was added during the washing step but only after the second ion-exchange step. After the removal of mother liquor, firstly one portion of Millipore Q water (using liquid to solid ratio of 20) was added and then a next portion of 0.01 M $NH_4OH$ solution using liquid to solid ratio of 40. The drying and calcination procedures were the same as used for Cat 6.

Cat 11 was prepared according to procedure given in example 1 for Cat 6 but the parent zeolite was $NH_4$ZSM-5 (SM27 supplied by Alsi Penta) instead of NaZSM-5 (SN27, Alsi Penta).

The properties of the catalysts Cat 9-Cat 11 are given in TABLE 2. Washing with $NH_4OH$ (cat 10) results in replacing of K-ions by $NH_4$-ions which are transformed after the calcination to $H^+$ increasing Brønsted acidity. When a $NH_4$-form of zeolite is used instead of a Na-form (cat 11), single ion exchange procedure is not sufficient to fully replace $NH_4$-ions by K, resulting in higher proton density.

Cat 12 was prepared according to the same procedure as Cat 9 but amount of Millipore Q water used for washing was reduced from liquid to solid ratio of 60 to 10. The drying and calcination procedures were the same as used for Cat 6.

Cat 13 was prepared according to the same procedure as Cat 10 but addition of KOH was performed during washing step. Washing was applied but only after the second exchange step. After the removal of mother liquor, firstly one portion of Millipore Q water was added (using liquid to solid ratio of 20) was added and then a next portion of 0.01 M KOH solution using liquid to solid ratio of 40. The drying and calcination procedures were the same as used for Cat 6.

The properties of the catalysts cat 12 and cat 13 are given in TABLE 2 showing the importance of a proper washing procedure. Poor washing lead to accumulation of the remaining salts in the pores or surface of the zeolite material (in this case K/Al molar ratio is above 1).

TABLE 1

Details of the exchange with potassium and sodium and physicochemical properties of the catalysts

| Catalyst | ion exchange: C (MNO3), M/LSR* | Exchange degree** | Brønsted acid density, μmol/g *** | Lewis acid density, μmol/g *** |
|---|---|---|---|---|
| Z = Parent zeolite | — | 0 | 5.6 | 174.8 |
| Cat 1 | 0.05M $KNO_3$/20 | 0.68 | 1.4 | 134.5 |
| Cat 2 | 0.1M $KNO_3$/20 | 0.85 | n/d | n/d |
| Cat 3 | 0.25M $KNO_3$/20 | 0.94 | 1.1 | 140.5 |
| Cat 4 | 0.5M $KNO_3$/20 | 0.97 | 0.5 | 121.9 |
| Cat 5 | 1M $KNO_3$/20 | 0.98 | 0.3 | 97.4 |
| Cat 6 | 1M $KNO_3$/40 | 1.00 | 0.0 | 81.1 |
| Cat 7 | 1M $NaNO_3$/40 | — | 2.9 | 228.1 |
| Cat 8 | 0.5M $NaNO_3$/20 (repeated 4 times) | — | 5.9 | 267.1 |

*LSR is liquid to solid ratio used for ion-exchange procedure
**exchange degree determined as K/(K + Na), measured by ICP-AES;
*** measured by FTIR of adsorbed pyridine;
n/d = not determined

TABLE 2

Physicochemical properties of the catalysts Na-free KZSM-5 with various proton density and various K/Al

| Catalyst | Exchange degree* | K/Al** Molar ratio | Brønsted acid density, μmol/g *** | Lewis acid density, μmol/g *** |
|---|---|---|---|---|
| Cat 9 | 1.00 | 0.97 | 0.0 | 74.4 |
| Cat 10 | 1.00 | 0.92 | 3.4 | 111.2 |
| Cat 11 | 1.00 | 0.93 | 2.1 | 119.4 |
| Cat 12 | 1.00 | 1.03 | n/d | n/d |
| Cat 13 | 1.00 | 1.01 | 0.0 | 102.5 |

*exchange degree determined as K/(K + Na), measured by ICP-AES;
**measured by ICP-AES;
*** measured by FTIR of adsorbed pyridine;
n/d = not determined Comparative Example 1 (LA Conversion, Impregnation with $KH_2PO_4$)

Figure 1B:
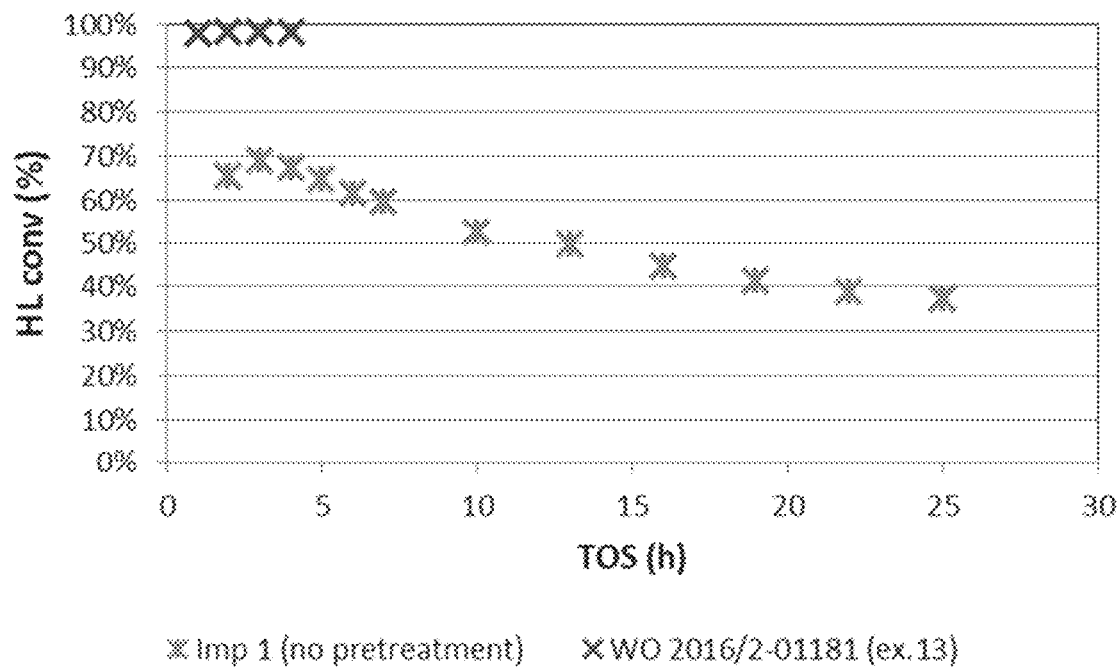
FIG. 1B shows the lactic acid conversion with comparative catalyst 1 A using conditions mentioned in WO 2016/201181 obtained in Comparative Example 1, wherein the open circles and shaded x-es refer to the data obtained in our measurements and the filled circles and black-x-es refer to the data provided in WO 2016/2-01181, respectively.
Figure 1C:
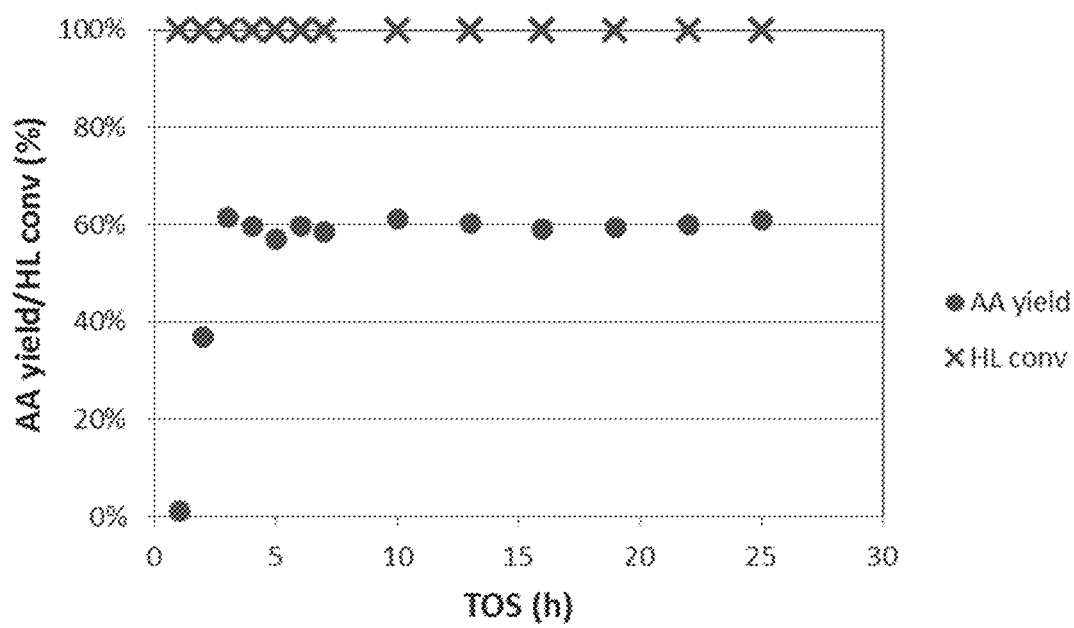
FIG. 1C shows the acrylic acid yield and lactic acid conversion for Na-ZSM5 catalyst using conditions mentioned in WO 2016/201181 obtained in Comparative Example 2.

Example 13 of the Myriant application WO 2016/2-01181 was re-worked. To this end 1 g of a commercially available Na ZSM-5 ex Alsi-Penta Zeolith GmbH with a $SiO_2/Al_2O_3$ molar ratio of 24 was impregnated with 4 mmoles of $KH_2PO_4$ by means of incipient wetness impregnation. The catalysts were dried and calcined at 250° C. and used in a lactic acid dehydration reactor using water as a solvent for the lactic acid. In order to do a fair comparison the Liquid Hourly Space Velocity (LHSV) was set to be 1.8 $h^{-1}$. The results are given in FIGS. 1A-B, wherein the open circles and shaded x-es refer to the data obtained in our measurements and the filled circles and black-x-es refer to the data provided in WO 2016/2-01181, respectively.

The catalyst testing has been performed under the reaction conditions of the Myriant application. The catalyst resulted in very poor performance, i.e. a low lactic acid conversion (initially 70%) and poor stability.

Comparative Example 2 (LA Conversion, No Impregnation)

Example 13 of WO 2016/201181 was re-worked as described in Comparative example 1, except that the catalyst was not impregnated with $KH_2PO_4$. As is clear from FIG. 10, both the acrylic acid yield (60%) and the full lactic acid conversion remained stable over time. The catalyst gave a better performance than the $KH_2PO_4$ impregnated catalyst of WO 2016/201181.

Comparative Example 3 (Methyl Lactate (ML)Conversion, Water)

The catalyst as prepared in comparative example 1 was used for the dehydration of methyl lactate using water as a solvent for the methyl lactate. The following reaction conditions were used: reaction temperature of 340° C., volume of the catalyst=1.7 ml, carrier gas ($N_2$) flow=10 ml/min; liquid feedstock: 35% methyl lactate (ML) in $H_2O$ pumped with the rate of 0.9 ml/h; LHSV=0.5 $h^{-1}$.

In FIG. 2 the results are given. These show that the catalyst described in example 13 of WO 2016/201181 when used for the conversion of methyl lactate to methyl acrylate in water shows a low conversion (below 50%), and a very low methyl acrylate yield.

Example 2. Dehydration of Methyl Lactate to Methyl Acrylate Using K-ZSM-5 Zeolite: Effect of Solvents Cat 5 (example 1) was used as a catalyst. The dehydration of 35 wt. % methyl lactate (ML) in various solvents or without the solvent has been performed as summarized in the TABLE 3. In all the cases, the amount of the methyl lactate (ML) passed over the catalyst bed was kept constant (WHSV) and concentration of methyl lactate in the gas stream was roughly the same.

TABLE 3

| Reaction conditions used for testing in example 2 | | | | |
|---|---|---|---|---|
| T = 340° C. Catalyst volume = 1.7 ml Catalyst weight = 1.0 g | MeOH | $xH_2O$—MeOH | $H_2O$ | No liquid solvent |
| Liquid feedstock composition | 35% ML/ 65% MeOH | 5% H2O = 35% ML/(3.25% $H_2O$—61.75% MeOH) 10% H2O = 35% ML/(6.5% $H_2O$—58.5% MeOH) 25% $H_2O$ = 35% ML/(16.25% $H_2O$—48.75% MeOH) 50% $H_2O$ = 35% ML/(32.5% $H_2O$—32.5% MeOH) | 35% ML/65% $H_2O$ | 100% ML |
| $N_2$ flow, ml/min | 10 | 10 | 10 | 16 |
| Feed flow rate, ml/min | 0.015 | 0.015 | 0.015 | 0.004 |
| ML concentration in total gaseous stream, mol. % | 5.7 | 5.2-5.7 | 4.8 | 5.3 |
| LHSV (total feed), $h^{-1}$ | 0.5 | 0.5 | 0.5 | 0.1 |
| WHSV (ML), $h^{-1}$ | 0.3 | 0.3 | 0.3 | 0.3 |

Figure 3A:
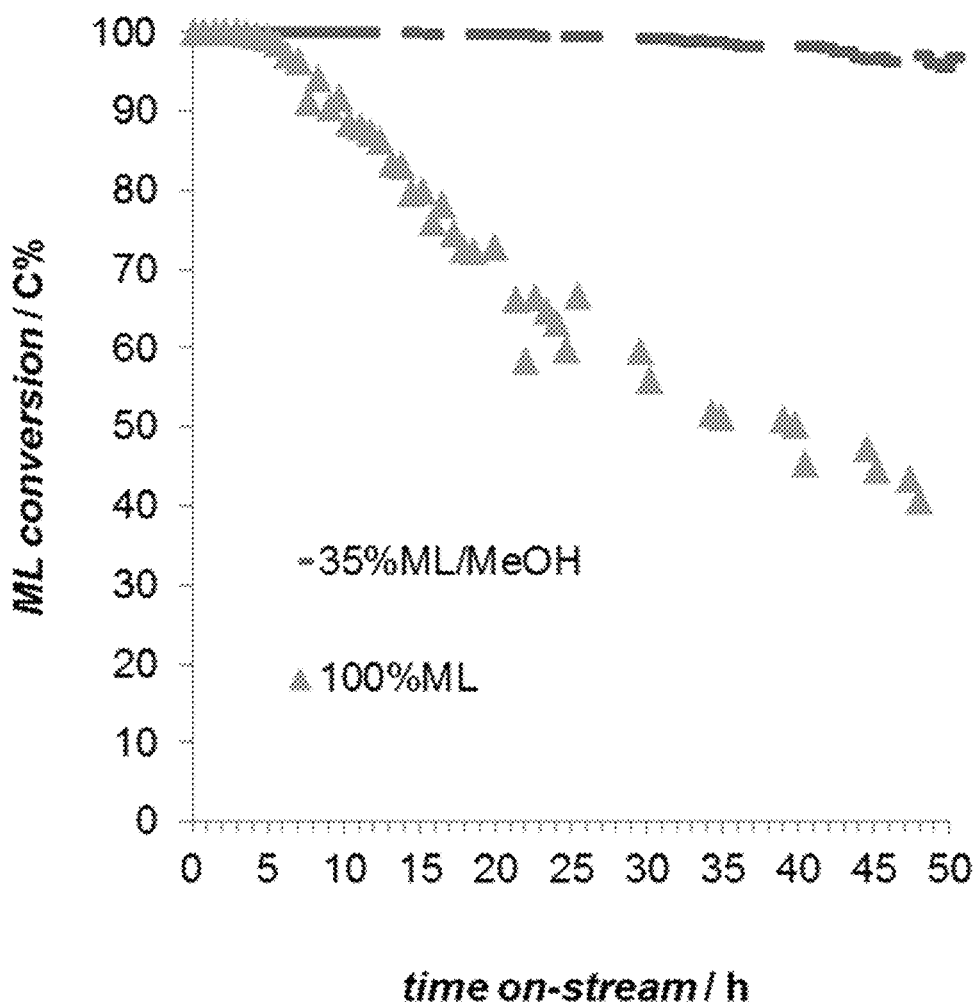
FIG. 3A shows the methyl lactate (ML) conversion of the KZSM-5 catalyst during 50 h time-on-stream obtained in Example 2.
Figure 3B:
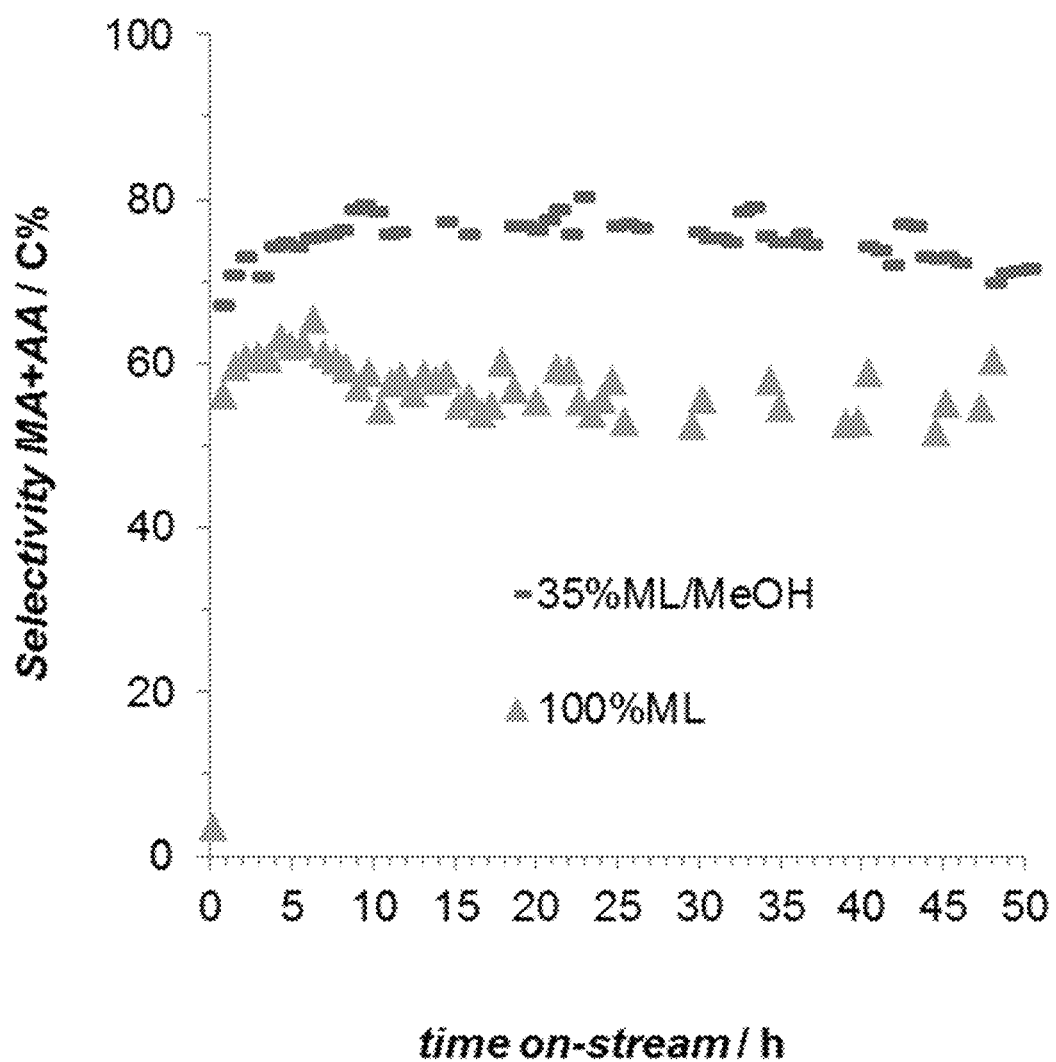
FIG. 3B shows the total acrylates selectivity of the KZSM-5 catalyst during 50 h time-on-stream obtained in Example 2.
Figure 3C:
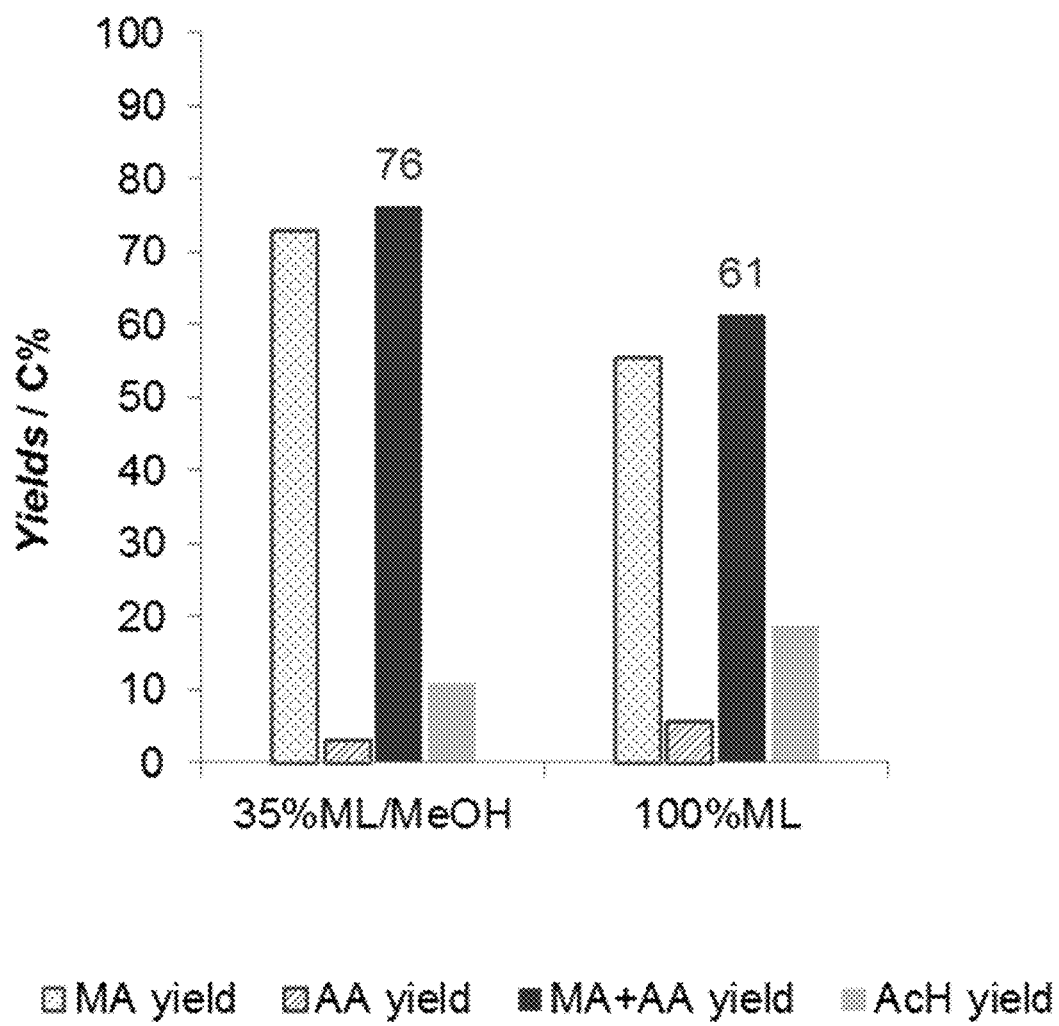
FIG. 3C shows the product distribution obtained in Example 2 (Yields are averaged within the period of stable acrylates (MA+AA) formation).

FIGS. 3A-C show the importance of the liquid solvent present in the liquid feedstock. In the absence of solvent (feeding 100% ML), the catalyst deactivates very fast and more acetaldehyde is being formed as a side-product.

Figure 3D:
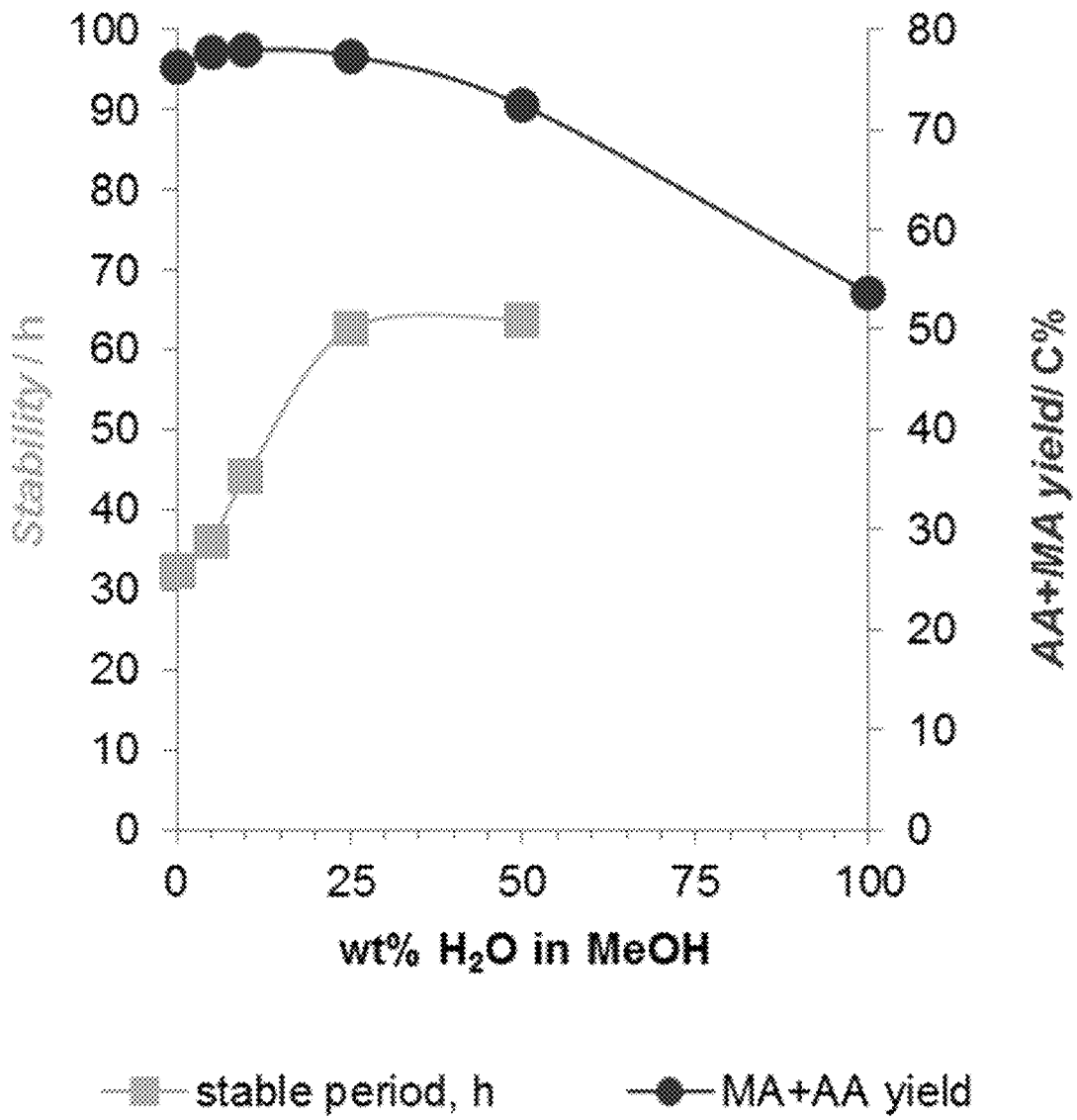
FIG. 3D shows the impact of the water content of selectivity and stability of the KZSM-5 catalyst (35% ML/solvent feed) obtained in Example 2.

FIG. 3D shows the impact of the water content in the liquid feedstock containing 35 wt. % ML. Presence of MeOH is essential. The use of water instead of methanol has a positive impact on the catalyst stability, however it has a detrimental effect on the total acrylate selectivity (54%) and the amount of methyl acrylate content produced (<50%). Presence of small amount of water up to 25% is advantageous for the catalyst performance namely for stability and total acrylates selectivity.

Example 3. Impact of the Exchange Degree on Dehydration of Methyl Lactate to Methyl Acrylate Using K-ZSM-5 Zeolites Catalysts prepared in example 1 were tested in methyl lactate (ML) conversion. The following reaction conditions were used: reaction temperature of 340° C., volume of the catalyst=1.7 ml, carrier gas ($N_2$) flow=10 ml/min; liquid feedstock: 35% (ML) in MeOH pumped with the rate of 0.9 ml/h; LHSV (total liquid feed)=0.5 $h^{-1}$. Full methyl lactate (ML) conversion was observed for all K-containing catalysts with exchange degree higher than 0.85 during first 24 hour time-on-stream while in case of parent zeolite the conversion dropped after 12 h time-on-stream. Progressive replacing of sodium cation by potassium cations led to a drop of acetaldehyde (AcH) yield in the favor of acrylates formation (both methyl acrylate and acrylic acid). A K-exchange degree above 0.97 (defined as K/(K+Na)) and a residual proton density essentially low (below 1 micromole/g) (cat 4, 5 and 6) are two parameters required to reach acrylates selectivity above 76 C % stable for at least 30 h time-on-stream (TABLE 4).

TABLE 4

Impact of K-exchange degree on catalytic performance of ZSM-5 catalyst (example 3)

| | stable period, h* | Maximum selectivity MA + AA, C % | ML conversion, C % | AcH selectivity, C % |
|---|---|---|---|---|
| Z = Parent zeolite | 4.9 | 58.0 | 100 | 21.1 |
| Cat 1 | 9.3 | 72.4 | 100 | 15.9 |
| Cat 2 | 18.2 | 74.8 | 100 | 12.6 |
| Cat 3 | 23.5 | 74.5 | 100 | 12.3 |
| Cat 4 | 31.2 | 76.0 | 100 | 11.1 |
| Cat 5 | 32.3 | 76.3 | 100 | 10.7 |
| Cat 6** | n/d | 80 | 100 | 11.0 |
| Cat 7 | 4.9 | 61.5 | 100 | 20.3 |
| Cat 8 | 4.2 | 59.1 | 100 | 21.0 |

*Stable period is defined as the timeframe in hours between the point when the maximum total acrylates yield reached and the point when total acrylates yield declines for more than 2 C % from maximum yield;
**no long time-on-stream tests were performed (experiment was stopped after 24 h run)

Example 4 Comparison of Potassium-Exchanged and Sodium-Exchanged Catalyst

Attempts were made to decrease the residual Brønsted acidity by ion-exchange with sodium nitrate to have an accurate comparison with proton-free potassium ZSM-5. To this end, Na parent ZSM-5 was subjected to ion exchange with sodium nitrate both at room temperature and 4-step exchange at elevated temperature. The preparation conditions of these catalysts, Cat 7 and Cat 8 are compiled in TABLE 1.

However, neither single step exchange at room temperature nor four step exchange at 80° C. could eliminate completely the Brønsted acid sites. The following reaction conditions were used: reaction temperature of 340° C., volume of the catalyst=1.7 ml, carrier gas ($N_2$) flow=10 ml/min; liquid feedstock: 35% Methyl lactate (ML) in MeOH pumped with the rate of 0.9 ml/h; LHSV (total liquid feed)=0.5 $h^{-1}$. No significant impact was observed from additional Na-ion-exchange on catalytic performance.

Figure 4A:
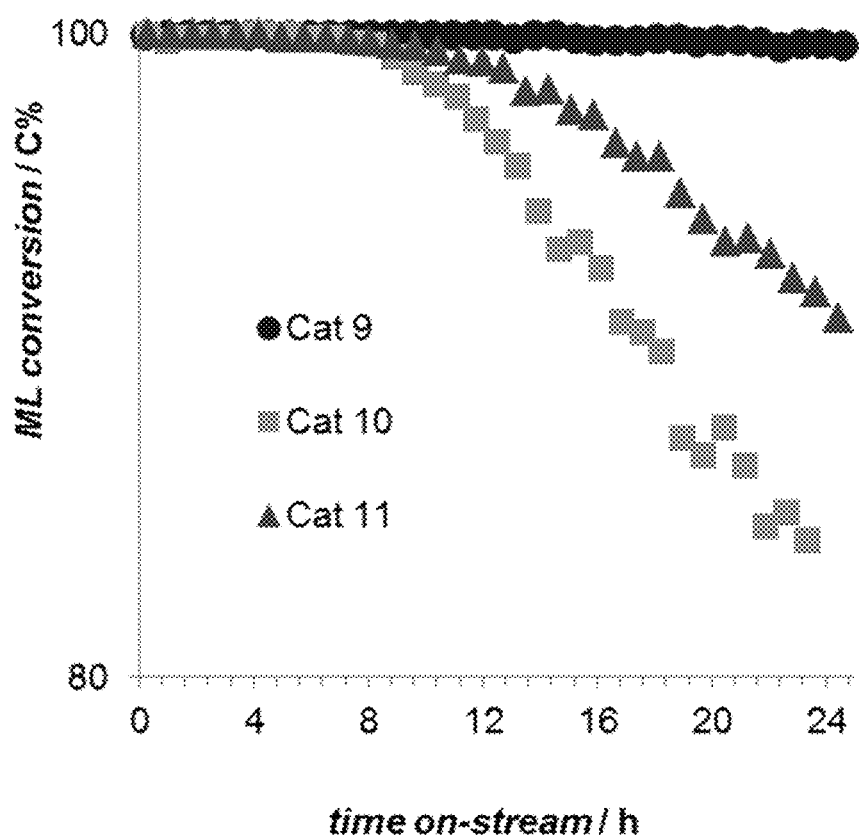
FIG. 4A shows the methyl lactate (ML) conversion obtained in Example 5.
Figure 4B:
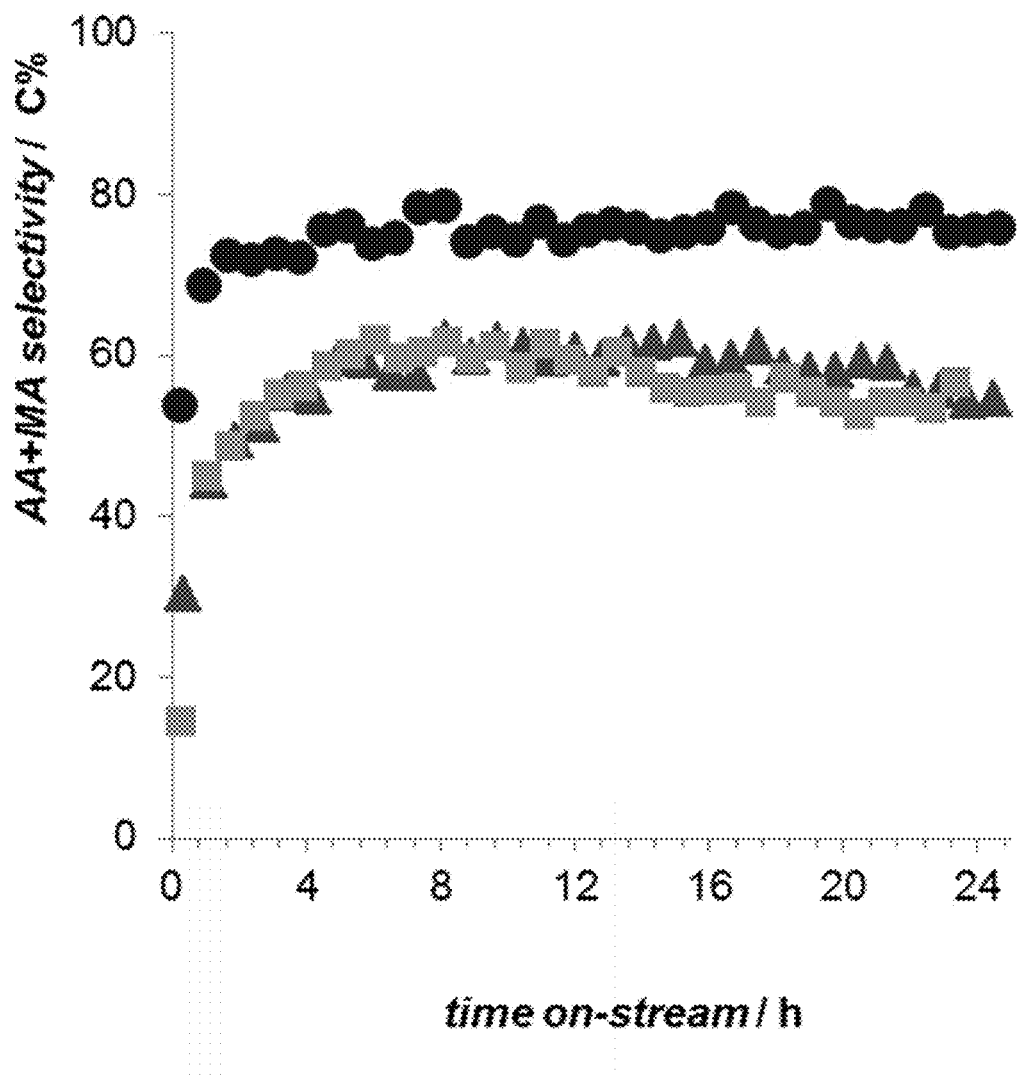
FIG. 4B shows the total acrylates selectivity over the KZSM-5 catalyst during 24 h time-on-stream, influence of proton density obtained in Example 5.

Example 5 Impact of the Proton Density on Dehydration Methyl Lactate to Methyl Acrylate Using K-ZSM-5 Zeolites A series of Na-free K-ZSM-5 catalysts with varied proton density prepared according to example 1 (Cat 10-11) were tested. The following reaction conditions were used: reaction temperature of 340° C., volume of the catalyst=1.7 ml, carrier gas ($N_2$) flow=10 ml/min; liquid feedstock: 35% Methyl lactate (ML) in MeOH pumped with the rate of 0.9 ml/h; LHSV=0.5 $h^{-1}$. FIGS. 4A-4B show that time-on-stream behavior (both selectivity and activity) of the catalyst Cat 10 and Cat 11 having higher proton density is poor compared to Cat 9 with proton density below 1 micromole/g. High proton content leads to poor stability and selectivity.

Figure 5A:
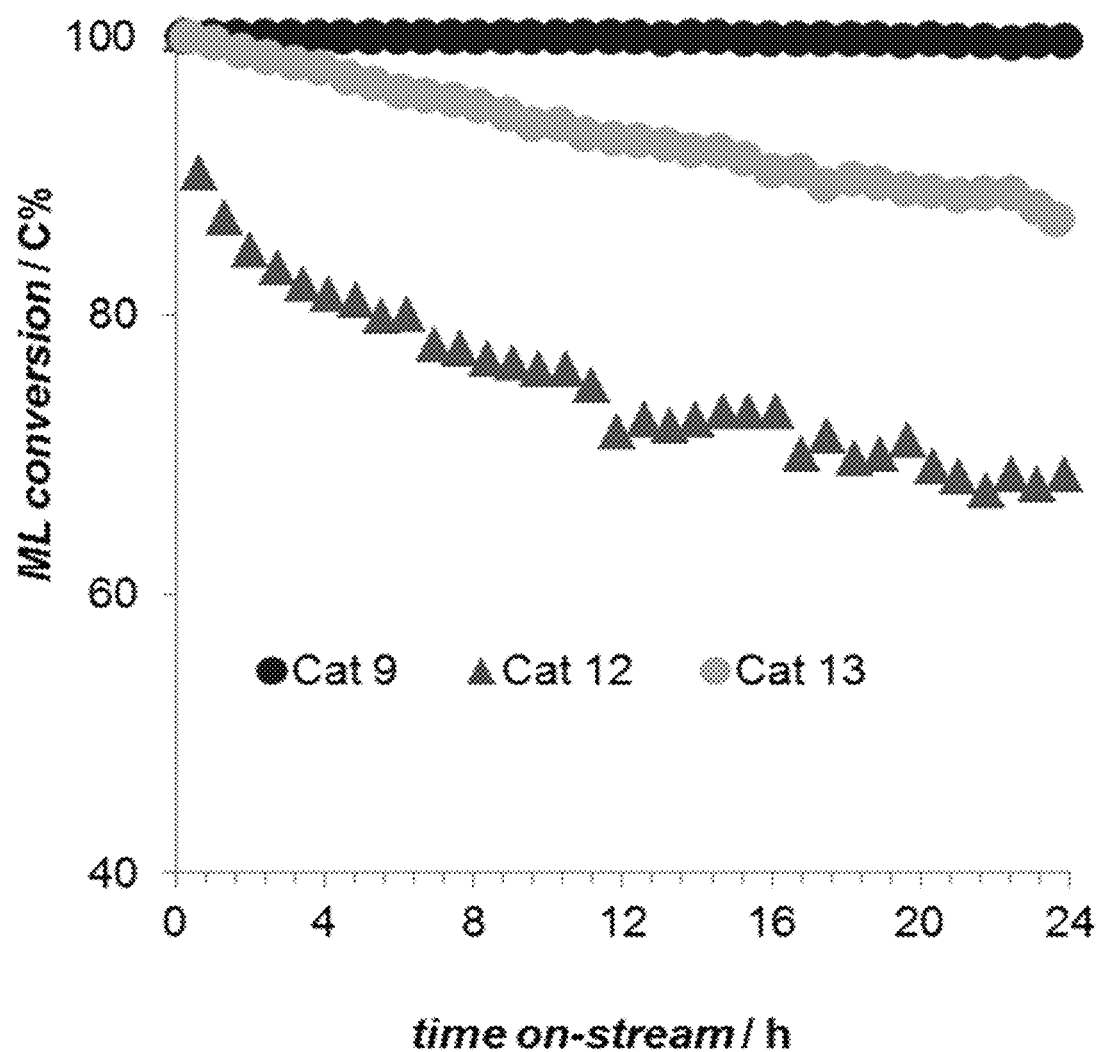
FIG. 5A shows the methyl lactate (ML) conversion obtained in Example 6.
Figure 5B:
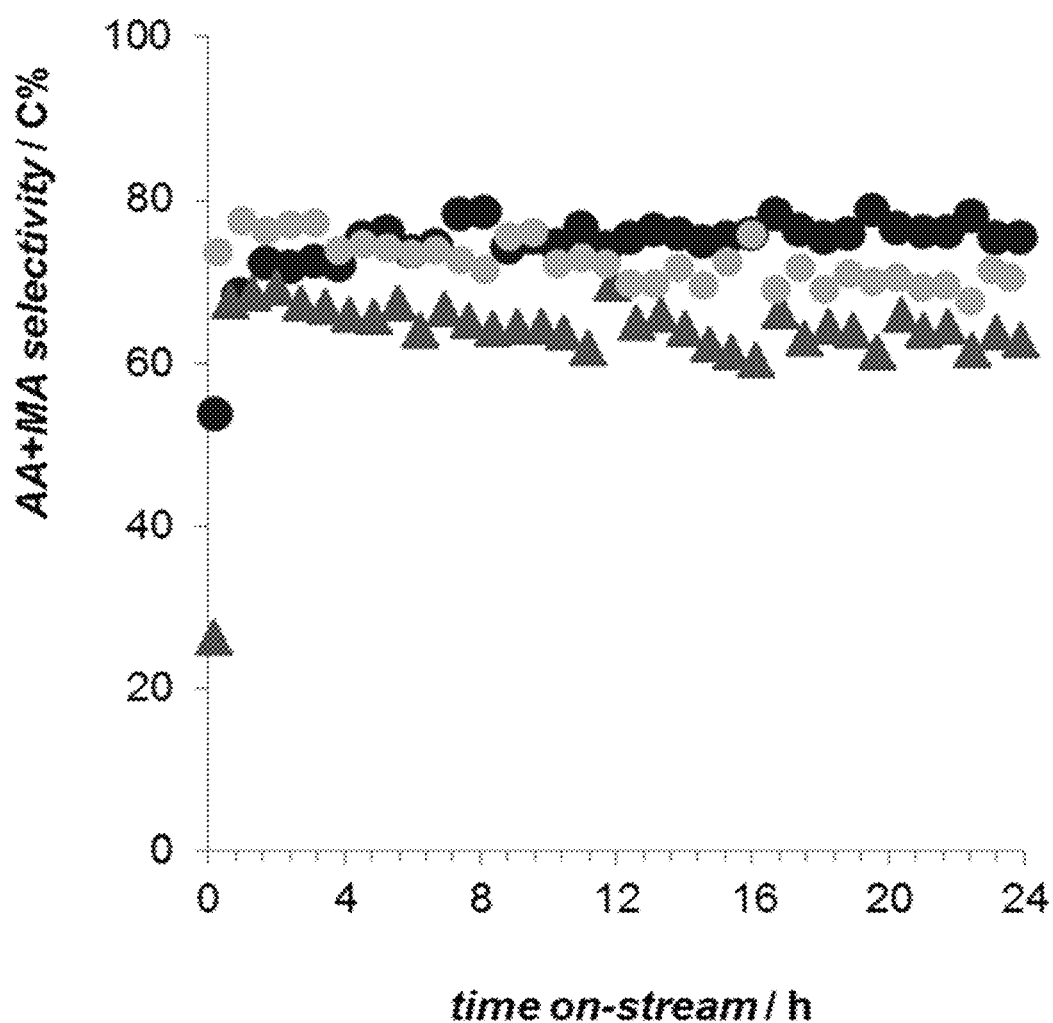
FIG. 5B shows the total acrylates selectivity over the KZSM-5 catalyst during 24 h time-on-stream, influence of K/Al molar ratio obtained in Example 6.

Example 6 Impact of the K/Al Molar Ratio on Dehydration Methyl Lactate to Methyl Acrylate Using K-ZSM-5 Zeolites A series of catalysts with excess of potassium prepared according to example 1 (Cat 12-13) was tested. The following reaction conditions were used: reaction temperature of 340° C., volume of the catalyst=1.7 ml, carrier gas ($N_2$) flow=10 ml/min; liquid feedstock: 35% Methyl lactate (ML) in MeOH pumped with the rate of 0.9 ml/h; LHSV=0.5 $h^{-1}$. FIGS. 5A-5B show that time-on-stream behavior (both acrylates selectivity and activity) of the catalyst Cat 12 and Cat 13 having K/Al molar ratio above 1 is poor compared to properly washed Cat 9.

Example 7 Impact of the Feedstock on Performance of K-ZSM-5 Zeolites

K-ZSM-5 catalyst (Cat 5) with low proton density (below 1 micromole/g) and having K/Al molar ratio of about 1.00 was tested also in lactic acid (LA) conversion and results were compared with methyl lactate (ML) conversion. Both reactions were performed under similar reaction conditions (LHSV of 0.5 $h^{-1}$), however in the ML conversion methanol was used as solvent, while in the lactic acid conversion water was used as a solvent. Results are presented on FIG. 6 showing that deactivation of the catalyst in methyl lactate (ML) conversion is more pronounced compared to acid (LA). Thus, overall performance of the catalysts is substrate dependent.

The invention claimed is:

1. A process for the production of methyl acrylate comprising as step of contacting methyl lactate with a ZSM-5 catalyst in the presence of methanol.

2. The process according to claim 1, wherein the methanol is used as a solvent.

3. The process according to claim 1, wherein the ZSM-5 catalyst comprises $SiO_2$ and $Al_2O_3$ and a $SiO_2/Al_2O_3$ molar ratio of the ZSM-5 catalyst is between 10 and 30.

4. The process according to claim 1, wherein the ZSM-5 catalyst is a potassium-salt ion exchanged ZSM-5 catalyst.

5. The process according to claim 4, wherein the starting material for potassium salt ion exchange is a sodium-based ZSM-5 catalyst.

6. The process according to claim 4, wherein a degree of potassium exchange is higher than 0.90.

7. The process according to claim 1, wherein an amount of Brønsted acid sites in the ZSM-5 catalyst is below 1 micromole/g, as measured by FTIR on absorbed pyridine.

8. The process according to claim 1, wherein an amount of Lewis acid sites on the ZSM-5 catalyst is between 50 and 130 micromole/g, as measured by FTIR on absorbed pyridine.

9. The process according to claim 4, wherein the ZSM-5 catalyst comprises potassium and aluminum and a K/Al molar ratio of the catalyst is between 0.95 and equal to 1.00.

10. The process according to claim 1, wherein the phosphorus content of the ZSM-5 catalyst is below 10 ppm.

11. The process according to claim 1, wherein the sulfur content of the ZSM-5 catalyst is below 10 ppm.

12. The process according to claim 1, wherein the catalyst has been prepared by ion-exchanging a sodium-, hydrogen- or ammonium form of ZSM-5 with a potassium salt and then washing, drying and calcining the ion-exchanged catalyst.

13. The process according to claim 12, wherein the ion exchange salt is potassium nitrate or potassium chloride.

14. The process according to claim 1, wherein a methyl lactate solution in methanol, evaporated in inert gas is continuously led over a fixed catalyst bed, and a product stream is isolated, separated and purified.

15. The process according to claim 1, further comprising processing the resulting methyl acrylate using one or more distillation steps, extraction steps or any combination thereof.

16. The process according to claim 1, further comprising a step of hydrolyzing the methyl acrylate into acrylic acid.

17. The process according to claim 16, further comprising processing the acrylic acid using one or more distillation steps, extraction steps or any combination hereof.

18. The process according to claim 1, wherein the methanol is used as a solvent in combination with between 1 and 25 wt. % of water, based on the total amount of the solvent.

19. The process according to claim 4, wherein a degree of potassium exchange is higher than 0.95.

20. The process according to claim 1, wherein an amount of Lewis acid sites on the ZSM-5 catalyst is between 86 and 100 micromole/g, as measured by FTIR on absorbed pyridine.

\* \* \* \* \*